(12) United States Patent
Larkin

(10) Patent No.: US 6,975,392 B2
(45) Date of Patent: Dec. 13, 2005

(54) ENHANCED SENSITIVITY DIFFERENTIAL REFRACTOMETER MEASUREMENT CELL

(75) Inventor: Michael I. Larkin, Santa Barbara, CA (US)

(73) Assignee: Wyatt Technology Corporation, Santa Barbara, CA (US)

( * ) Notice: Subject to any disclaimer, the term of this patent is extended or adjusted under 35 U.S.C. 154(b) by 155 days.

(21) Appl. No.: 10/768,600

(22) Filed: Jan. 29, 2004

(65) Prior Publication Data

US 2005/0168733 A1  Aug. 4, 2005

(51) Int. Cl.$^7$ .............................................. G01N 1/10
(52) U.S. Cl. ........................ 356/246; 356/128; 356/73
(58) Field of Search ........................ 356/246, 128–136, 356/337–343, 73; 250/573–575

(56) References Cited

U.S. PATENT DOCUMENTS

| | | | |
|---|---|---|---|
| 4,286,873 A * | 9/1981 | Carson ........................ | 356/130 |
| 4,728,190 A * | 3/1988 | Knollenberg ................ | 356/336 |
| 4,952,055 A * | 8/1990 | Wyatt .......................... | 356/73 |
| 6,774,994 B1 * | 8/2004 | Wyatt et al. ................. | 356/337 |

* cited by examiner

Primary Examiner—Gregory J. Toatley, Jr.
Assistant Examiner—Sang H. Nguyen
(74) Attorney, Agent, or Firm—Philip J. Wyatt

(57) ABSTRACT

A sensitivity-enhanced flow cell to be used in the determination of the differential refractive index increment of a sample fluid relative to a reference fluid is disclosed. The invention permits the use of smaller sample amounts without sacrificing overall sensitivity. Equally important, said improved flow cell produces measurements of increased precision without requirement for increased sample amount. This is achieved by means of two chambers within said cell whose volumes are different. The sample fluid chamber is the smaller of the two with the reference fluid chamber constructed so that the incident illumination beam, upon passage through said sample chamber and displacement by the partition element located therebetween said sample and reference chambers, passes through said reference chamber without grazing any of the confining walls or striking corners of said sensitivity-enhanced flow cell. As the amount of deflection of said transmitted beam depends upon the refractive indices of the fluids relative to the transparent matter of which the containing cell is comprised, as well as the RI difference between said fluids themselves, the reference chamber is designed to transmit said incident light beam without grazing degradation thereof for all practical ranges of expected fluid and cell refractive indices.

14 Claims, 3 Drawing Sheets

ENHANCED SENSITIVITY DIFFERENTIAL REFRACTOMETER MEASUREMENT CELL

RELATED AND CO-PENDING APPLICATIONS

Expressly incorporated herein are the following related patents and concurrent applications. These are of importance as the present invention insures that they may be used and implemented more effectively:

U.S. Pat. No. 4,616,927—"Sample Cell for Light Scattering Measurements," (Oct. 14, 1986)

U.S. Pat. No. 5,530,540—"Light scattering measurement cell for very small volumes," (25 Jun. 1996)

U.S. Pat. No. 6,411,383—"Method for measuring the $2^{nd}$ virial coefficient," (25 Jun. 2002).

U.S. Pat. No. 6,651,009—"Method for determining average solution properties of macromolecules by the injection method," (Nov. 18, 2003)

Ser. No. 10/665,903 filed 18 Oct. 2003, S. Trainoff, "Method for Correcting the Effects of Interdetector Band Broadening."

Ser. No. 10/723,548 filed 25 Nov. 2003, M. Larkin, "Refractometer Cell for both Absolute and Differential Refractive Index Measurement of Fluids."

BACKGROUND

The difference in refractive index between a sample and a reference material is referred to as the differential refractive index, dRI, and is a physical parameter of considerable importance. The dRI between a sample solution consisting of a solvent plus a solute and a reference solution comprised of a pure solvent may be used to determine the solute concentration from the relation $$\Delta c \approx \Delta n \Big/ \left(\frac{dn}{dc}\right),$$

where the change in concentration, $\Delta c$, is directly proportional to the measured change in solution refractivity, $\Delta n$. The constant of proportionality is the reciprocal of the differential refractive index increment, $$\frac{dn}{dc}.$$

A typical instrument for measuring the dRI is a "walk-off" type differential refractometer. That instrument contains a cell made of a transparent material with two fluid chambers, able to accommodate either a liquid or a gas, and having an angled transparent interface separating the chambers. As pictured in FIG. 1, a beam of light 1 passes into the cell, through sample chamber 2, through the interface 3 separating the two chambers, through reference chamber 4, and finally out of the cell. For the cell pictured, if the fluids in the two chambers have identical indices of refraction, then after exiting the cell the transmitted beam of light 5 travels in a path parallel to the incident beam 1. If the two fluids have different indices of refraction, then the transmitted beam of light 6 travels in a path which is at some angle θ to the incident beam. The angle θ between the incident light beam and the transmitted light beam is, to first order, proportional to the difference in refractive index between the two liquids. That angular deflection of the light beam may be measured by a variety of well established techniques, and so the dRI may be measured and reported.

Although the incident beam, as shown in FIG. 1, strikes the sample chamber interface normal to the entrance surface, in general, the incident beam will be oriented at an angle to it. In this manner, for example, it becomes possible to have the finally transmitted beam reflected by a mirror back into the flow cell chambers so that exits through the same surface. By such mirror means the sensitivity of the cell will be doubled. The emerging beam will not be parallel to or co-linear with the incident beam and may be detected more easily.

Conventionally, the angle of the transparent interface between sample and reference chambers is of the order of 45° with respect to the direction of the incident beam, though the greater this angle is the greater will be the angular deflection of the transmitted beam due to the difference between refractive indices of the sample and reference fluids. For the geometry shown, increasing this angle results in a requirement for a sample fluid chamber of increased volume while decreasing it decreases the angular deflection due to the refractive index difference between the sample and reference fluids.

Applications which utilize measurements of the dRI between two liquids typically benefit if the amount of sample required for a measurement is reduced. For many applications, sample preparation requires a great expenditure of time and resources, and reducing the quantity of sample required for measurements has a direct financial benefit. In addition to a reduction of costs and effort associated with sample preparation, the quality of measurements are in many cases enhanced if the quantity of sample required for a measurement is reduced. Liquid chromatographic systems are one example where the quality of the measurements are in some cases enhanced if the volume of sample required for measurement is reduced. In a liquid chromatographic system a material potentially consisting of many species is dissolved into a solvent and then injected into a fluid stream. The fluid stream is made to traverse some medium or device which preferentially delays species in the medium or device based upon some physical parameter, such as size, chemical affinity, thermal properties, electrical properties, etc., and so separates the species from one another. The different species thus exit the medium or device at different times. In keeping with traditional nomenclature, this medium or device will here be referred to as a column, although the physical form and function of the device may be quite different from a column. The fluid passing through the column typically exits into a small diameter tube, and so at any one moment in time different species reside at different locations along the length of the tube. If a measurement device, such as a differential refractometer, is situated such that the fluid flows from that tube through the measurement device, then the species which make up the material may be individually measured. The measurement of constituent species of a material is an essential purpose of chromatographic systems. Since a finite volume of liquid is always required for measurement, the species within some volume of the tube necessarily contribute to the signal at any moment in time. The measurement device is therefore always measuring an average over the species which reside along the length of the tube which corresponds to the measurement volume. This averaging over species negates in part the separation accomplished by the column, and results in a reduction in the quality of data. Reducing the volume of sample required for measurement minimizes the averaging over species, resulting in higher quality data.

In addition to the negative effects on data quality due to the measurement averaging over a finite volume of sample, some volume of sample is mixed together as it traverses the measurement system. Many chromatographic systems consist of several measurement devices placed serially along the fluid stream, each measuring different physical parameters concerning the sample. If a measurement device mixes some volume of fluid together, then all subsequent measurements on that fluid are negatively impacted by the resulting averaging over multiple species in the measurement volume. Typically, the larger the volume required for measurement, the larger the volume of sample which is mixed together, and the greater the negative impact on data quality for instruments placed later in the fluid stream.

In addition to their application in the field of liquid chromatography, differential refractometers of various types are used in many different fields. By accurately determining refractive index differences between a reference standard and a sample, such determinations may be used to determine sucrose concentration, fluid densities, the concentrations of a myriad of industrial fluids such as sulfuric acid, sodium chloride, ethanol, etc. A variety of instruments have been designed around the concept of measuring and using such refractive index differences as a means to measure various derivative quantities.

There are clearly advantages in reducing the volume of sample required for a dRI measurement. However, for a walk-off type differential refractometer, a tradeoff exists between reduction of the sample volume and sensitivity of the dRI measurements. There are at least three reasons for a reduction in dRI sensitivity with a reduction in sample volume. The first reason for a reduction in sensitivity is a reduction in averaging over the sample. For even perfectly stable systems, fundamental laws of thermodynamics predict local fluctuations through time of the temperature, density, and solute concentrations across the sample and reference liquids. This was explained at length by Albert Einstein in his 1910 seminal paper on "The theory of opalescence of homogeneous fluids and liquid mixtures near the critical state," published in Annelen der Physik, volume 33, pages 1275–1298. Real world systems are never perfectly stable, and those fluctuations are in general enhanced in real systems. Those fluctuations cause the path of the light beam traversing the fluids to change through time, and so cause the angle θ at which the light beam 6 exits the cell to fluctuate with time. The fluctuations through time of the beam angle are seen as noise in the dRI measurement. Increasing the volume sampled by the beam causes the beam to better average over these local fluctuations, reducing their overall effect.

A second reason that a reduction in sample volume results in a reduction in sensitivity of the dRI measurement is a reduction of optical power through the system. For the cell design picture in FIG. 1, as the sample volume is reduced, the area of sample through which light may be sent is reduced. To obtain the same optical power through the system, the light intensity must be increased. Typically, a system used to measure the angular deflection of the light beam has its sensitivity increase in some proportion to the optical power supplied to it. Therefore, to obtain with a smaller volume sample the same sensitivity in the determination of the beam angular deflection as with a larger volume sample, the light intensity must be increased. Since these systems are typically already using the most intense light sources practicable, a reduction in sample volume necessarily results in a reduction of optical power through the system and a corresponding reduction in the sensitivity with which the angular deflection of the light beam may be determined. A reduction in the sensitivity with which the angular deflection of the light beam may be determined corresponds directly to a reduction in sensitivity of the dRI measurement.

A third way that reducing sample volume reduces sensitivity of the dRI measurement is once again due to a reduction in the area through which the light beam may be sent. As the area through which the light beam is sent is reduced, diffraction effects limit the sharpness with which the beam may subsequently be focused. The smaller the area through which the beam passes, the more diffuse the focal point becomes. Typically, a system used to measure the angular deflection of the light beam has its sensitivity increase as the sharpness of the focused beam increases. And so yet again reducing the area through which the light beam passes results in a decrease in sensitivity in determining the beam angular deflection, corresponding to a reduction in sensitivity of the dRI measurement.

It is an important objective of my invention to increase the sensitivity of a dRI measurement while at the same time minimizing the amount of sample required. Another objective of my invention is to reduce diffraction effects by increasing the dimension of the clear aperture through which the beam must pass without increasing the sample volume. A further objective is to provide for a broad range of instrument response without the beam moving too closely to any side of the cell.

BRIEF DESCRIPTION OF THE INVENTION

In order to achieve the objectives of this invention, a new type of cell for a dRI instrument is disclosed. Rather than integrate a conventional structure comprised of two juxtapositioned chambers of approximately the same size, the novel cell of the invention employs chambers of two different sizes. The first chamber containing the sample solution, and into which the incident beam first enters the cell, is smaller that the successive chamber containing the reference fluid. Before entering the sample cell, the incident beam passes through a mask limiting its cross section to fill the sample chamber while not passing too closely to the chamber edges. In the preferred embodiment of the invention, the two chambers have cross sections comprised of similar triangles with the reference chamber made large enough to accommodate all beam displacements at the interface/partition separating the two chambers. The reference chamber is made large enough so that the displacement of the beam passing through the interface between the chambers will not strike or graze the edges of said reference chamber for a large range of liquid refractive indices. These include fluids whose refractive indices are less than the refractive index of the glass or transparent material of which the cell is fabricated as well as fluids whose refractive indices are great than said cell materials. In this manner, the invention allows a reduction of the sample volume without compromising the sensitivity of the dRI measurement, or conversely an increase in sensitivity without increasing the sample volume.

DETAILED DESCRIPTION OF THE INVENTION

The objective of all dRI detectors is to measure the refractive index difference between the reference and sample fluids. For a walk-off type dRI detector, this is accomplished by measuring the angular deflection of the light beam emerging from the cell after traversing it. The translation of the emerging beam relative to the incident beam contributes to limit the sensitivity of the conventional cell structure by reducing the region within the sample chamber which may be illuminated and still have that light reach and traverse the reference chamber. This translation has a major dependence upon the refractive index difference between the sample fluid refractive index and that of the transparent material of which the cell is fabricated, and a minor dependence on the refractive index difference between the sample and reference fluids. For most practical applications, especially those related to the field of liquid chromatography, the refractive index between the two fluids is small compared to that between the fluids and the cell material.

Figure 1:
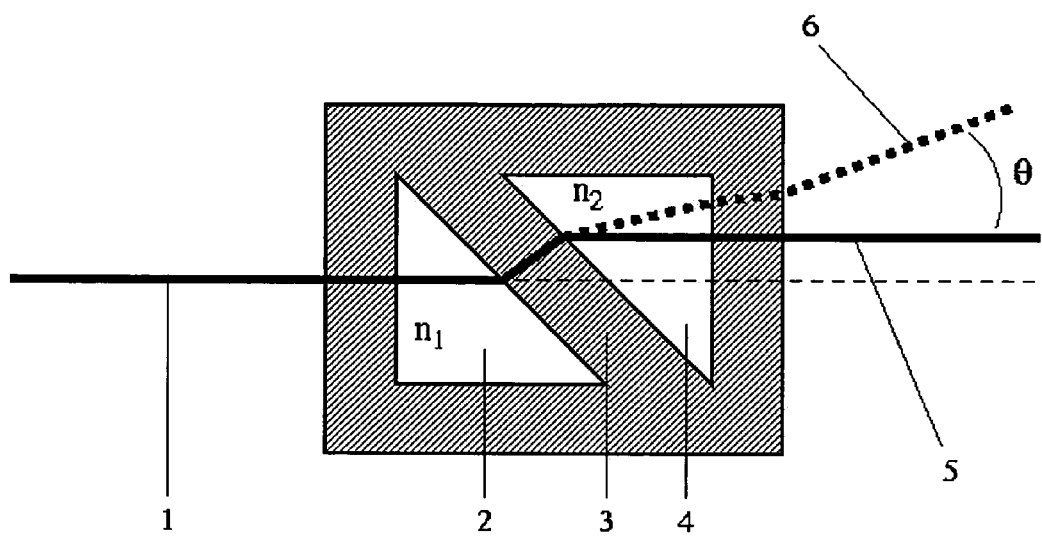
FIG. 1 shows a conventional dRI cell design illustrating the displacement of the transmitted beam.
Figure 2:
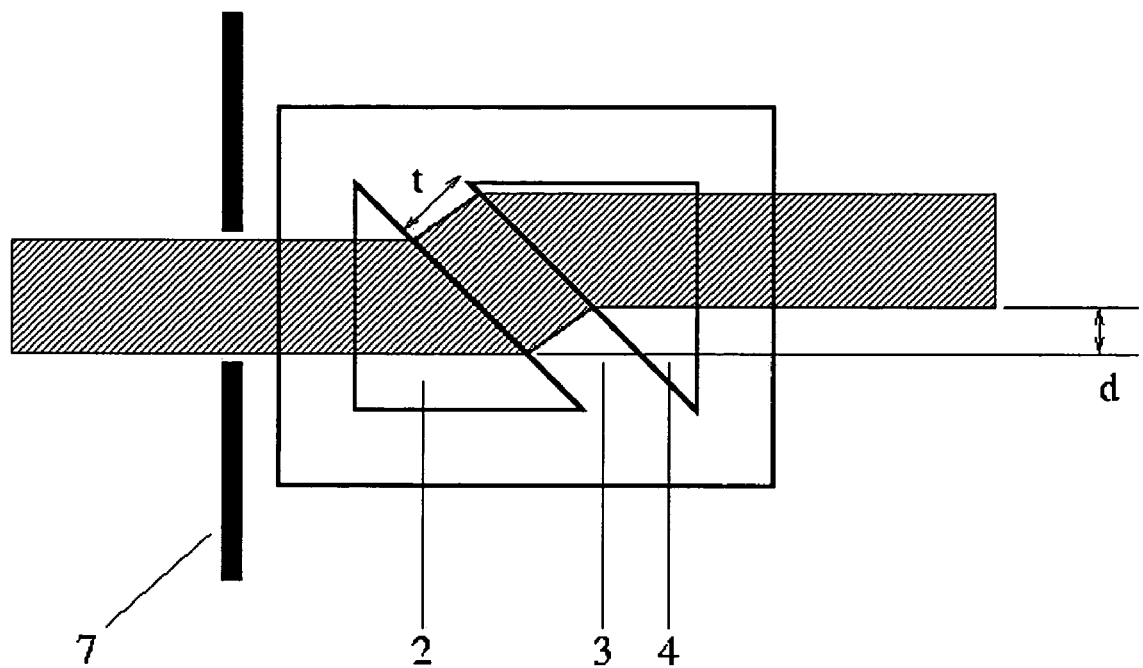
FIG. 2 shows a conventional cell with the beam filling most of the sample chamber.

FIG. 1 shows a very thin light beam for purposes of clarity. The cell when filled with as much light as possible, for the reasons discussed in the background section, is shown in FIG. 2. Note that the beam undergoes a translation d as it passes through the partition 3 of thickness t between the sample and reference chambers. That translation need not contribute to the dRI measurement, since using simple optics it is possible to separate angular deflection of the beam from its translation. However, that translation does limit the volume within the sample chamber which may usefully be illuminated. Light near the edges of the sample chamber 2 could miss the reference chamber 4, and thus not contribute to the measurement, reducing, thereby, its sensitivity. If light is allowed to enter the sample chamber 2 that misses or grazes the reference chamber, it will reflect and scatter from various surfaces, corners, and discontinuities of the cell typically contributing, thereby, a spurious and undesirable signal to whatever device is measuring the angular deflection of the light beam. To prevent that situation, an aperture 7 is typically placed before the flow cell, as shown in FIG. 2, ensuring that light which would miss or graze the reference chamber 4 is not permitted to enter the sample chamber 2.

The direction of the translation depicted in FIG. 1 and in FIG. 2 is appropriate when the index of refraction of the fluid is less than the index of refraction of the material comprising the cell. That is the common case, but in some instances the fluid to be measured has a higher index of refraction than that of the cell material. For example, a fluid such as toluene has an index of refraction of 1.5 that is greater than a typical cell material made of fused silica, with an index of refraction of 1.46. Since dRI detectors are typically designed to operate with a variety of fluids, the aperture is made small enough and positioned such that, over the desired range of fluid refractive indices, no light will graze the reference chamber walls. For a typical low volume type flow cell, the light beam may be restricted to enter only the central 65% of the sample chamber 2; the rest of the chamber being essentially unused, but nevertheless filled with sample fluid. It is the thickness of the partition 3 that results in a translation of the light beam, and the negative consequences described above associated with that translation. As the thickness of the partition is brought to a negligible thickness, the translation goes to zero, as do the consequences associated with the grazed surfaces of the reference chamber 4. However, it is practically difficult to make that dimension small. Furthermore, as the partition dimension is reduced, pressure differences between the sample and reference chambers cause the partition between them to flex, adding noise and distortion to the measurement. Pressure differences inevitably exist between the sample and reference chambers, especially in the case where fluid is flowing through one or both chambers.

Figure 3:
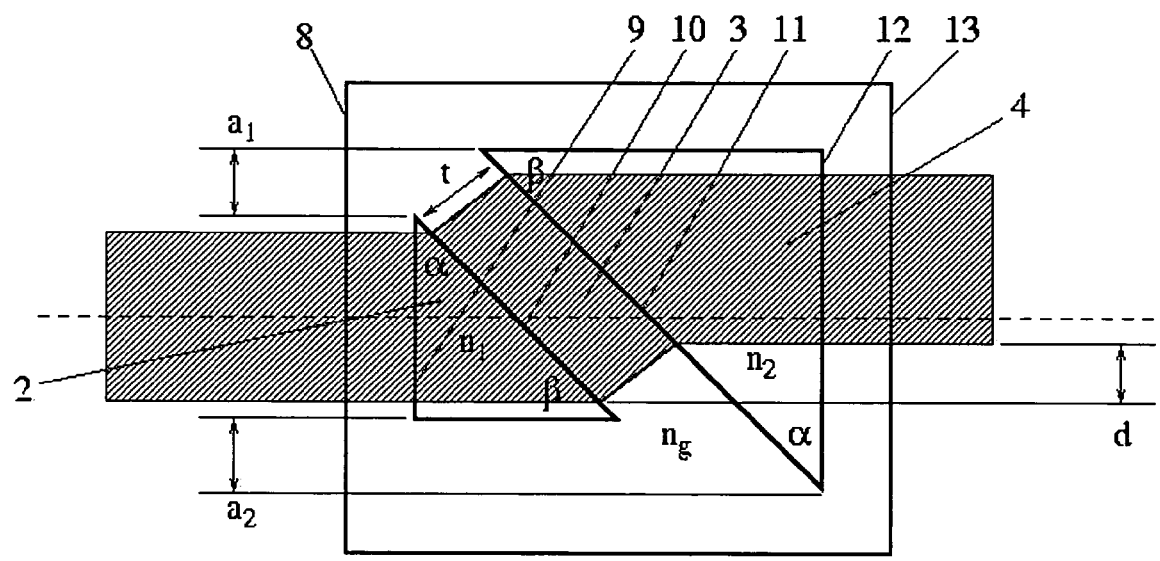
FIG. 3 shows the preferred embodiment cell of the present invention.

The reference chamber 4 of the invention, whose preferred embodiment is shown in FIG. 3, is made sufficiently larger than the sample chamber to allow the light beam to traverse said reference chamber without impinging on any of its corners located at the intersections of said chamber's faces, nor grazing any side through which said beam is not intended to pass after said beam has entered the sample chamber 2 at any position along face 9, traversed the sample chamber, and passed onto and through the partition 3 into said reference chamber. This allows the full volume of the sample chamber to be illuminated by the incident beam. As the fraction of the sample chamber volume illuminated is increased, the sensitivity of the measurement is increased without increasing the size of the sample chamber. Conversely, using the invention described, the sample volume may be made smaller than in a conventional flow cell with no loss in measurement sensitivity since, in the preferred embodiment, a greater fraction of the sample chamber volume is illuminated. For conventional chromatographic measurements, the reference chamber 4 is filled with a reference fluid at the beginning of a measurement and then sealed during the course of the measurement. Thus an increase in volume of the reference chamber 4 does not affect the volume of the sample required for a measurement.

The degree by which the flow cell reference chamber 4 must be made larger than the sample chamber depends upon the physical details of the flow cell and the range of solvent refractive indices to be measured. For any embodiment, the reference chamber 4 must be made large enough and positioned correctly for the light incident anywhere in the sample chamber 2 to successfully reach and traverse the reference chamber. In FIG. 3 we show a preferred embodiment of the invention. In this embodiment, the reference chamber 4 has a triangular cross section which is a similar triangle to the sample cell cross section. The planes 8, 9, 12, and 13 are parallel to one another, and the planes 10 and 11 are parallel to one another. The sample and reference chambers are separated from one another by a partition of thickness t, and the light beam depicted is translated by a distance d due to passage through the partition. The fluid in the sample chamber has refractive index $n_1$, that in the reference chamber has refractive index $n_2$, and the partition between the sample and reference chambers has refractive index $n_g$. The refractive index difference between the sample and reference fluids $n_1$ and $n_2$ is typically of the order of $1 \times 10^{-3}$ or less, while that between $n_1$ or $n_2$ and $n_g$ is of the order of 0.1. For the purposes of simplifying the derivation below, we will assume $n_1 \approx n_2 \equiv n_f$. With this assumption, the translation d may be seen to be:

$$d = t\sin(\alpha)\left\{1 - \frac{m\cos\alpha}{\sqrt{1-m^2\sin^2\alpha}}\right\}, \text{ where } m = n_l/n_g,$$

Note that in the case when the liquid has a higher refractive index than the transparent material of the cell, i.e. m>1, d is negative and the beam displacement is downward.

For the conventional embodiment of the invention shown in FIG. 3 to accept a range of fluid refractive indices $m_{max}>1.0>m_{min}$, the length of side 12 must be greater than the incident beam width by at least $a_1+a_2$, where $a_1=d(m_{min})$ and $a_2=-d(m_{max})$ are the dimensions indicated in FIG. 3. Here $m_{max}$ is the maximum value of the refractive index ratios anticipated and $m_{min}$ is the smallest. From a practical point of view, the largest m will be of the order 1.5/1.46= 1.03, corresponding to toluene in a fused quartz cell. The smallest m would be of the order of 1.33/1.62=0.82, corresponding to water in a cell made of F2 glass. Taking α of the order of 45°, we have the requirement for a downward increase of side 12 by $a_2=0.023$ t and an upward increase by $a_1=0.29t$. If t is a typical value of 1.0 mm, the reference chamber wall 12 need be about 0.29+0.023=0.313 mm longer than the sample chamber. A conventional embodiment of a refractometer cell may have a sample chamber dimension of 1.4 mm, and so the reference chamber of the corresponding preferred embodiment of the invention shown in FIG. 3 is made at least 22% larger than a 1.4 mm sample chamber, and allows for a 22% increase in the illuminated area of the sample chamber.

The above conditions are required for the beam of light, impacting the partition between the sample and reference chambers anywhere on the sample side, to enter the reference chamber successfully, i.e. without grazing the cell edges or being truncated thereby. The derivation above was specific to the geometry of the conventional embodiment of FIG. 3, and given the assumption that $n_1 \approx n_2 \equiv n_l$. However it will be clear to those skilled in the art of differential refractive index measurements that relaxing the assumption of $n_1 \approx n_2$ adds somewhat to the complexity of the equations above, and adds the requirement that the reference chamber be expanded further to account for translation of the beam as it traverses the reference chamber due to angular deflection of the beam, resulting from the differential refractive index $\Delta n = n_1 - n_2$.

Calculation is not the only method by which the appropriate dimensions and placement of the reference cell may be determined. It is possible to determine the dimensions and placement of the reference cell by experimental methods, such as measurement of all pertinent angular deflections and translations over the range of interest of all pertinent indices of refraction and wavelengths. It is also possible to determine the dimensions and placement of the reference cell by computer simulation, using well established optical simulation techniques.

It will be clear to those skilled in the art that any technique or device which incorporates an incident beam of light that is not perpendicular to the partition between two fluid chambers will result in a translation of that light beam in some proportion to the refractive index difference between the fluids and the material comprising the partition. It should be evident also that for virtually every range of fluid refractive indices, the fraction of the fluid in the sample chamber illuminated by the incident beam may be maximized by enlarging the reference chamber relative to said sample chamber. My invention permits, thereby, an increase of instrument sensitivity without increasing the size of the sample required. Conversely, the sample size required to provide an accurate measure of its refractive index difference relative to that of the reference fluid may be decreased significantly by increasing the fraction of said sample illuminated by said incident beam. The greater the fraction of the sample illuminated within the sample chamber, the greater will be the sensitivity of the dRI detector to refractive index difference between sample and reference.

In the field of liquid chromatography, the dRI detectors discussed in the section on background are generally also used to determine sample concentration once the differential refractive index, dn/dc, has been measured. For such measurements used in conjunction with multiangle light scattering measurements, in addition to the need to measure the instantaneous concentration of samples eluting following fractionation by column or other means, the quantity dn/dc itself is an essential element of subsequent determinations of molar mass and size. Since dn/dc, and more generally the refractive index of all materials, changes as a function of the wavelength of light, measurement of both dn dc and concentration by such detectors is generally required at the same wavelength as the light scattering measurement itself. Thus the light beams frequently employed in such dRI detectors are monochromatic and designed to operate at the same wavelength as used to make the associated light scattering measurements.

There is, of course, no truly monochromatic light source, which is defined as a light source having a single perfectly defined wavelength. In the context of this patent disclosure a "monochromatic" light source corresponds to a light source having a range of wavelengths which is narrow enough that over such range of wavelengths, dn/dc of the solute in solution as well as the index of refraction of sample and reference fluids and the material comprising the cell changes by an amount which is acceptable for a particular application. For example, a "monochromatic" light source in this context may have a range of wavelengths over which the value of dn/dc changes by less than 1%, and all pertinent indices of refraction change by less than 0.01%. A laser may produce a range of wavelengths which is less than 1 nm while a non-lasing light emitting diode may have a range of wavelengths of 30 nm, but both may meet the above criteria for "monochromatic." Although the preferred embodiment of this invention would employ such monochromatic light beams, there are other applications of dRI detectors for which the dRI detector light sources are not monochromatic. Indeed, some commonly used dRI detectors employ so-called white light sources producing a light beam made up of contributions from a broad range of wavelengths or even just a few.

As has been described in considerable detail, the conventional implementation of a differential refractometer cell as shown, for example, in FIG. 1 includes two identical right triangular chambers. Extending this conventional structure to enhance the sensitivity of the device results in a structure similar to that shown in FIG. 3 wherein the two chambers are not identical but remain, nevertheless, of similar triangular cross sections. My invention, however, does not require that the triangles be similar nor does it require that the exit plane 13 be parallel to the entrance plane 8. Accordingly, there is no restriction that the chambers be of right triangular cross section. Indeed in my earlier co-pending application, "Refractometer Cell for both Absolute and Differential Refractive Index Measurement of Fluids," Ser. No. 10/723, 548, the exit plane defined by the two surfaces 12 and 13 includes an inner surface 12 that is not parallel to surface 13. The reference sample chamber cross section is not even a right triangle. Such a pair of dissimilar chambers provides means to measure the refractive index of fluids directly. Key to the success of my invention is the requirement that the exiting beam of light, after having passed into and through said reference chamber, passes out of said reference chamber through an exit face such as 13. The acceptable traversal of said reference chamber by the incident beam requires that said chamber must be of structure sufficient larger than the sample chamber to prevent said traversing beam from grazing boundaries thereof. The beam translation, d, as presented above, may be determined for any form of exit surface, including a wedged plane form as used for my aforereferenced co-pending refractometer application.

The fabrication and implementation of my inventive refractometer cell requires consideration of the following key elements:

1. A sample chamber whose smaller volume, and its correspondingly smaller sensitivity, is compensated by illuminating as much of the contained sample as possible without grazing the containing walls thereof: The sample chamber preferentially should have an entrance surface on which the incident light beam falls after having been restricted by aperture or other means and should have also an exit surface through which said light beam may pass after traversing said sample. Said exit surface should be at an angle to said traversing beam to insure the refraction of said beam as it passes into a reference chamber and to provide a boundary separating said sample chamber from said reference chamber. The greater said angle with respect to the direction of propagation of said light beam, the greater will be the angular deflection of the exit beam for a given refractive index difference between the sample and reference fluids.

2. A reference chamber, generally of size greater than said sample chamber, whose dimensions are determined by first establishing the maximum range of fluid refractive indices that will be employed in any measurement anticipated by said refractometer and then determining the corresponding range of beam displacements corresponding thereto; all constituent beam elements corresponding to said displacements exiting said chamber and cell via an exit surface without grazing other containing boundaries therein.

There are many embodiments of my invention that will be obvious to those skilled in the art of differential refractive index measurements that are but simple variations of my basic invention herein disclosed. Accordingly,

I claim:

1. A sensitivity-enhanced differential refractometer flow cell comprised of
   a) An aperture (7) restricting an incident light beam (1) that falls onto an entrance face (8) of
   b) A sample chamber (2), said restricting aperture limiting said incident beam to illuminate fully sample solution contained in said sample chamber (2) of said flow cell without impinging or grazing corners between defining sides of said sample chamber nor sides upon which said beam should not be incident;
   c) A transparent partition (3) through which said incident light beam (1) passes, after having traversed said sample chamber (2), into
   d) A reference chamber (4) containing a reference fluid and bounded by said transparent partition (3) separating said sample chamber (2) from said reference chamber (4) whose dimensions are established prior to fabrication by
      i. first determining the complete range of transmitted beam refractions at said partition interface (3), based upon the refractive index of said flow cell and the complete range of sample and reference refractive indices for which said enhanced-sensitivity refractometer flow cell will be, used, and then
      ii. providing adequate dimensions of said reference chamber (4) such that said transmitted beam is restricted to said reference chamber exiting it only at an exit face (13) and not grazing other surfaces or corners therein.

2. The sensitivity-enhanced differential refractometer flow cell of claim 1 where said incident light beam is monochromatic.

3. The sensitivity-enhanced differential refractometer flow cell of claim 1 where said sample and reference chambers are of similar right triangular cross sections.

4. The sensitivity-enhanced differential refractometer flow cell of claim 1 where said reference chamber exit surfaces (12) and (13) are plane surfaces which are not parallel.

5. The sensitivity-enhanced differential refractometer flow cell of claim 1 where said transparent partition (3) through which said incident light beam (1) passes, after having traversed said sample chamber (2), is not normal to said incident beam.

6. The sensitivity-enhanced differential refractometer flow cell of claim 1 where said transparent partition (3) is at an angle of the order of 45° with respect to said incident light beam direction.

7. The sensitivity-enhanced differential refractometer flow cell of claim 1 where said determination of the complete range of transmitted beam refractions is achieved by calculation based upon said refractive index of said flow cell and the complete range of sample and reference refractive indices for which said enhanced-sensitivity refractometer flow cell will be used.

8. The sensitivity-enhanced differential refractometer flow cell of claim 1 where said determination of the complete range of transmitted beam refractions is achieved by direct measurement of said transmitted beams for all sample and reference fluids for which said enhanced-sensitivity refractometer flow cell will be used.

9. A method for designing a differential refractometer flow cell of enhanced sensitivity for subsequent manufacture comprising the steps of
   a) Designing an incident light beam means to impinge upon an entrance face means of a sample chamber means (2) within said flow cell,
   b) Designing an aperture (7) restricting said incident light beam such that it illuminates fully a sample solution contained in said sample chamber (2) means without impinging or grazing corners between defining sides of said sample chamber nor sides upon which said beam should not be incident; said design
   c) Including a transparent partition means (3), separating said sample chamber (2) from an adjacent reference chamber that is to contain a reference fluid, through which said incident light beam (1) passes, after having illuminated said sample chamber (2),
   d) Determining the complete range of transmitted beam refractions at said partition means (3), based upon the refractive index of said flow cell means and the complete range of sample and reference solution refractive indices for which said enhanced-sensitivity refractometer flow cell will be used, e) Designing said reference chamber (4) of adequate dimensions, position, and structure such that said light beam entering thereinto through said partition means (3) is totally contained within said reference chamber, exiting it only at an exit face (13) and not grazing other surfaces or corners therein.

10. The design method of claim 9 where said incident light beam means chosen is monochromatic such that said sample and reference fluid refractive indices are determined at the wavelength of said monochromatic beam.

11. The design method of claim 9 where said transparent partition means (3) through which said incident light beam (1) passes, after having traversed said sample chamber means (2), is not normal to said incident beam.

12. The design method of claim 11 where said transparent partition means (3) is at an angle of the order of 45° with respect to said incident light beam direction.

13. The design method of claim 9 where said determination of said range of transmitted beam refraction is made via calculation of said transmitted beams for all sample and reference fluids for which said enhanced-sensitivity refractometer flow cell will be used.

14. The design method of claim 9 where said determination of said range of transmitted beam refraction is made direct measurement of said transmitted beams for all sample and reference fluids for which said enhanced-sensitivity refractometer flow cell will be used.

* * * * *